(12) United States Patent
Garth

(10) Patent No.: US 7,470,243 B2
(45) Date of Patent: Dec. 30, 2008

(54) PROGRESSIVE FLEXIBLE TABS ON ORTHOTIC DEVICES

(76) Inventor: Geoffrey C. Garth, 34 57th Pl., Long Beach, CA (US) 90803

(*) Notice: Subject to any disclaimer, the term of this patent is extended or adjusted under 35 U.S.C. 154(b) by 693 days.

(21) Appl. No.: 10/104,310

(22) Filed: Mar. 22, 2002

(65) Prior Publication Data

US 2003/0181838 A1      Sep. 25, 2003

(51) Int. Cl.
*A63F 5/00* (2006.01)
(52) U.S. Cl. .................................. 602/18; 128/DIG. 23
(58) Field of Classification Search .................. 602/18, 602/17, 19; 128/DIG. 23
See application file for complete search history.

(56) References Cited

U.S. PATENT DOCUMENTS

| | | | | |
|---|---|---|---|---|
| 5,097,824 A | * | 3/1992 | Garth | 602/18 |
| 5,366,438 A | * | 11/1994 | Martin, Sr. | 602/5 |
| 5,797,713 A | * | 8/1998 | Tweardy et al. | 411/339 |
| 5,830,167 A | * | 11/1998 | Jung | 602/19 |
| 5,993,403 A | * | 11/1999 | Martin | 602/18 |
| 6,090,058 A | * | 7/2000 | Traut et al. | 602/18 |
| 6,663,581 B1 | * | 12/2003 | Calabrese | 602/18 |
| 6,726,643 B1 | * | 4/2004 | Martin | 602/18 |

* cited by examiner

*Primary Examiner*—Fenn C Mathew
(74) *Attorney, Agent, or Firm*—Fish & Associates, PC

(57) ABSTRACT

The orthotic device for the restraint of a portion of the human body has flexible tabs at the edges of its principal panel. The flexible tabs are substantially rectangular in outline to maximize support area, but are tapered in cross-section substantially between the base and tip or otherwise configured to increase the flexibility of the tabs toward the tip to aid in comfort at the transition.

6 Claims, 3 Drawing Sheets

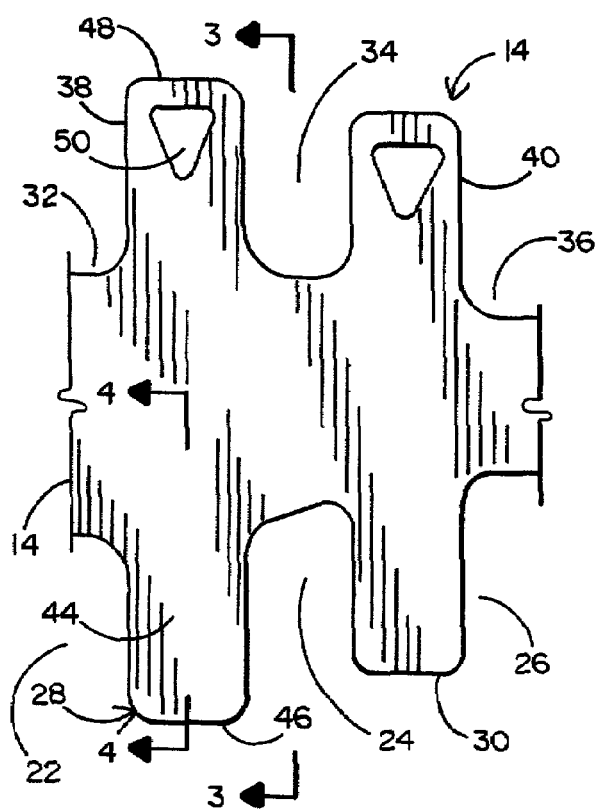
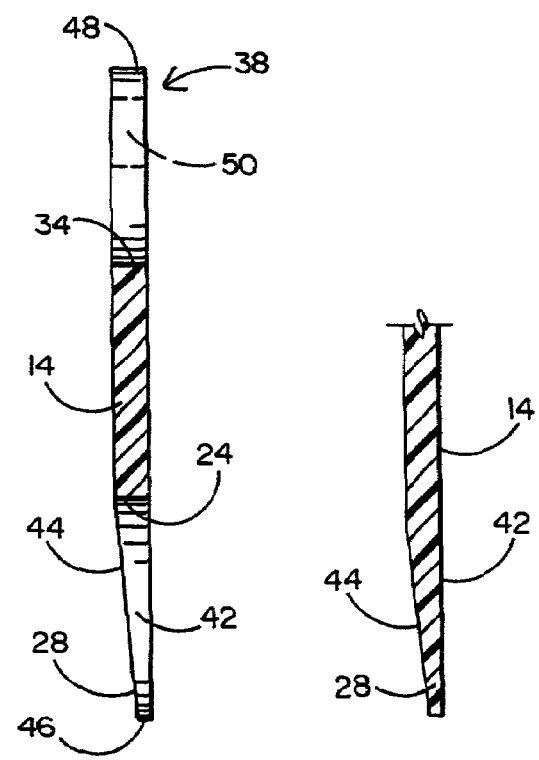
FIG. 2      FIG. 3      FIG. 4

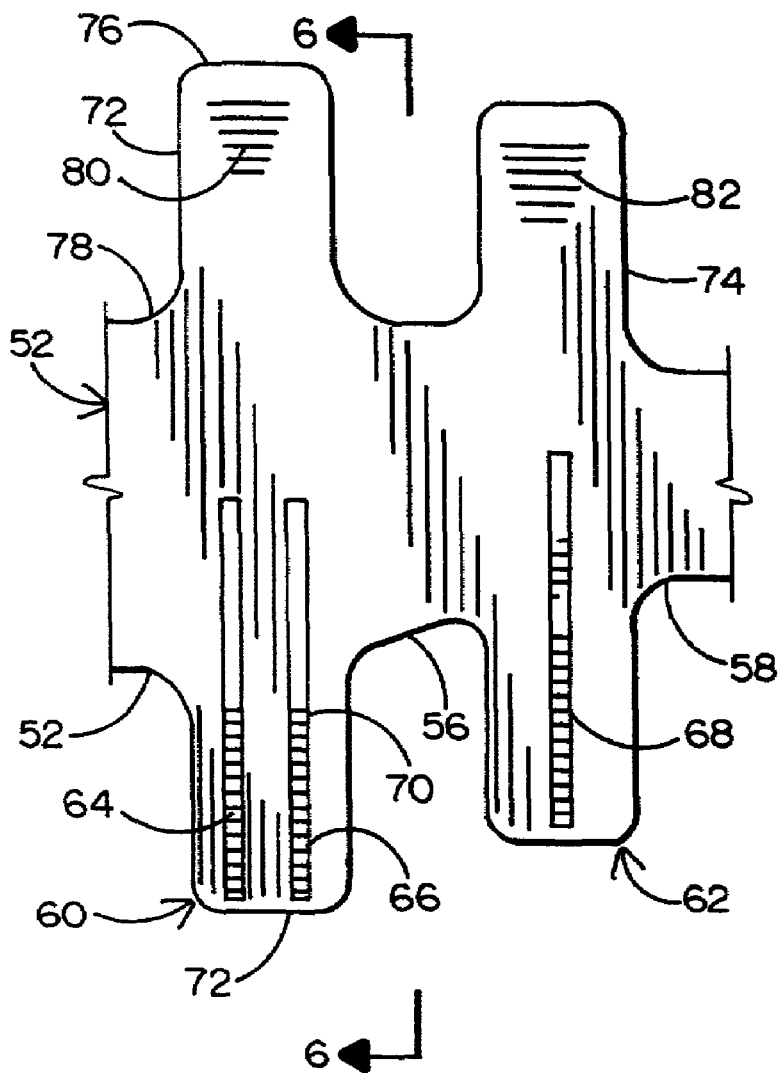
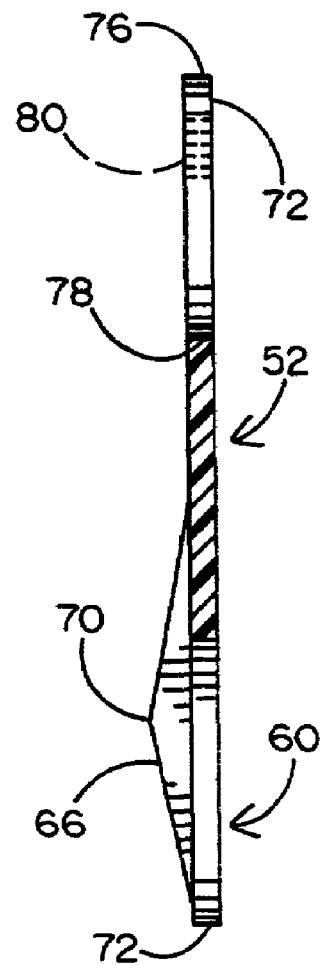
FIG. 5
FIG. 6

PROGRESSIVE FLEXIBLE TABS ON ORTHOTIC DEVICES

FIELD OF THE INVENTION

Orthotic devices are braces for engaging around a body part to restrict its mobility. The improvement is in the control of the flexibility at the edge of the orthotic device.

BACKGROUND OF THE INVENTION

The orthotic devices for which the progressive tabs of this invention are particularly useful have polymer sheet panels which are wrapped around the portion of the body to be stabilized. The panel edges are a transition between a restrained portion of the body and the unrestrained portion. The panel edges must be at least cushioned to prevent the panel edges from being painful to the patient and/or causing sores. Thus, configuration of the edges of the orthotic devices should be designed carefully to optimize the transition between restrained and unrestrained areas of the patient's body.

SUMMARY OF THE INVENTION

In order to aid in the understanding of this invention, it can be stated in essentially summary form that it is directed to progressive flexible tabs on orthotic devices. The orthotic devices have a polymer panel configured to at least partially engage around the body part to be restrained. The edges of the panel are notched to form tabs which are flexible to reduce the stiffness of the panel edges. In addition, the cross-section of the individual tabs decreases from the unnotched portion of the panel towards the free end of the tabs so that flexibility increases as compared to a tab having a uniform cross-section. Usually, the orthotic device has a foam polymer pad inside the panel to distribute loading on the body part.

It is, thus, a purpose and advantage of this invention to provide progressive flexible tabs on the edges of the orthotic devices so that the transition between the restrained and the unrestrained portions of the patient's body can be controlled.

It is another purpose and advantage of this invention to provide progressive flexible tabs at the edge of the polymer panel of the orthotic device and configure the cross-section of the tabs to control the flexibility of the tabs and thus the loading at the panel edges.

It is a further purpose and advantage of this invention to provide progressive flexible tabs in orthotic devices of various forms, including neck braces, body braces and the like.

Other purposes and advantages of this invention may be found in the following description, taken in conjunction with the accompanying drawings.

BRIEF DESCRIPTION OF THE DRAWINGS

FIG. 2 is a plan view, with parts broken away, of the polymer panel of the neck brace showing both the first and second preferred embodiments.

FIG. 3 is a section taken generally along line 3-3 of FIG. 2.

FIG. 4 is a section taken generally along line 4-4 of FIG. 2.

FIG. 5 is a plan view similar to FIG. 3 showing the third and fourth preferred embodiments of the progressive flexible tabs of this invention.

FIG. 6 is an enlarged view taken generally along line 6-6 of FIG. 5 showing the edge view of the third and fourth preferred embodiments.

DESCRIPTION OF THE PREFERRED EMBODIMENTS

Figure 1:
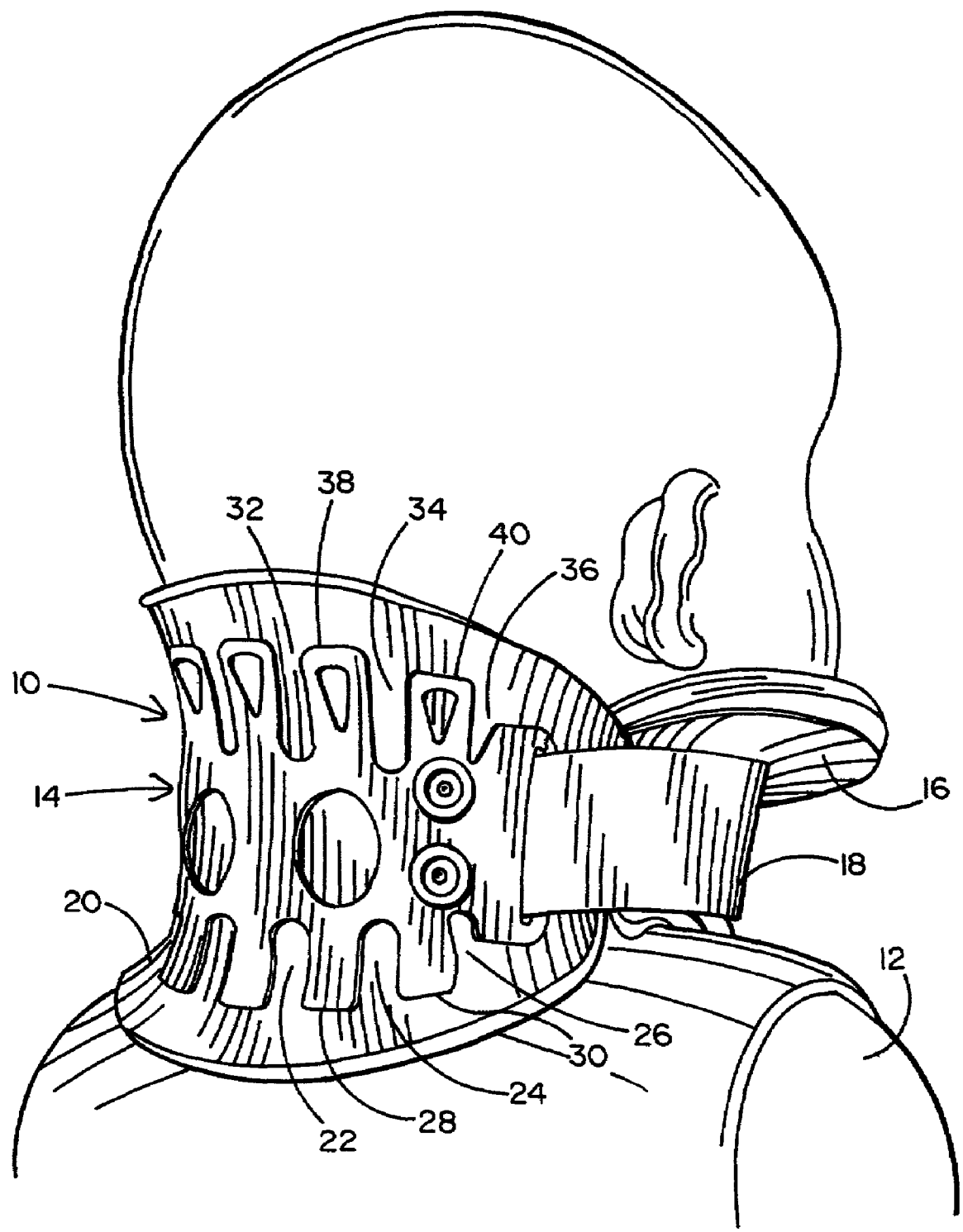
FIG. 1 is a perspective view of an orthotic device in the form of a neck brace as applied to a person showing the first and second preferred embodiment of the progressive flexible tabs of this invention.

The orthotic device 10 is an example of several different sizes and shapes of orthotic devices used for the stabilization of portions of the human body. In the present case, a child 12 has the orthotic device engaged around his neck. Such devices are often used when there has been physical stress on a person and it has not been determined if there is spinal injury. The orthotic device 10 is particularly configured for the child's neck. Other sizes and shapes of orthotic devices are available in child and adult sizes for stabilization of the back. The progressive flexible tabs of this invention are useful in different sizes of orthotic devices configured for the support of different body parts, and the particular orthotic device shown in FIG. 1 is just an example.

The orthotic device 10 comprise a panel 14 made of suitable synthetic polymer composition material, such as polyethylene, polypropylene or nylon. Thermoplastic materials are preferable because they can be formulated to have good flexibility. The panel 14 is of sheet material, but this does not necessarily mean it is of uniform thickness. In one embodiment, the panel is cut from a sheet of polymer material of uniform thickness and, in two other embodiments, the panel is molded so that it may have varying thickness.

The orthotic device 10 also has a chin support 16. It also has a tightening strap 18 which engages from one end of the panel to the other and engages under the chin support. Padding layer 20 underlies the panel 14 and is preferably a synthetic polymer foam panel such as a urethane foam. The padding layer is wider than the panel so as to cover the edges of the panel and aid in the support transition. The support transition is at the top and bottom edges of the panel where the panel no longer gives support. A padding layer of about 0.250 inch thickness is appropriate when the padding layer is a fairly stiff foam.

The panel 14 may be flat when it is not in service, but is wrapped around a portion of the body to provide orthotic support when it is in use. As seen in FIG. 1, the panel 14 is curved around an axis which is substantially parallel to the spine of the child 12, which is up and down in FIG. 1, parallel to the plane of the sheet. The polymer material from which the panel 14 is made is flexible, but not significantly resilient. This means it can bend around one axis, but not bend appreciably at the same time around a different axis. Consequently, when the panel 14 is curved around the upright axis, as shown in FIG. 1, the edges of the panel cannot bend away.

In order to permit such bending and to ease the load transition at the upper and lower edges of the panel, the panel is notched at the upper and lower edges. Notches 22, 24 and 26 are cut into the panel along its bottom edge to leave tabs 28 and 30 along the bottom edge. Similarly, notches 32, 34 and 36 are cut along the top edge to leave tabs 38 and 40. Such tabs are positioned all along the top and bottom edges of the panel. Since these tabs are small in circumferential direction (that is, along the length of the panel around the child's neck), the tabs can bend out away from the cylindrical curvature without significant distortion. This bending eases the transition of loading between the portion of the body constrained by the orthotic device 10, as compared to the body beyond the edges of the panel. The padding layer is principally filling which provides softness for comfort and does not provide significant support.

If the tab is rectangular in plan and of uniform thickness, the bending caused by the load of the padding layer onto the tab does not completely go to zero at the tip of the tab. The tab bends away from the loading, but the load does not uniformly decrease and is not zero at the tip of the tab.

A simple parabolic shape is believed to be the preferred curvature shape of the tab under load and this is not obtained by a tab of uniform cross-section. In order to achieve the parabolic shape, it is necessary to reduce the bending strength of the tab progressively away from the base of the tab towards its tip. It is desirable to maintain as much tab area as possible to provide transitional support. Thus, the tabs preferably have a substantially rectangular outline. The reduction in strength from the base of a tab to its tip is accomplished in the first preferred embodiment by tapering the tab to a thinner dimension toward the tip. As seen in FIGS. 3 and 4, tab 28 has a flat undersurface 42, which lies in a plane with the remainder of the inside surface of the panel 14 when the panel is laid out flat. The top surface 44 is tapered from the bottom of the notch 24 to the tip 46 of the tab. The taper of the top surface 44 is preferably uniform to substantially produce the desired parabolic shape when loaded. The width of the tab 28 is uniform, but the cross-section is reduced from base to tip by the taper of the tab. This is suitable for a molded panel 14. The other tabs along the lower edge of the panel 14 are of similar construction.

The tab 38 of the second preferred embodiment is of substantially uniform width and thickness from notch 34 to tip 48. In order to provide increasing flexibility from base to tip, tab 38 has a triangular hole 50. The triangle is an isosceles triangle with its base close to the tip 48 and its apex towards the base of the tab at the bottom of the adjacent notches. Theoretically, the triangle should have its apex at the base of the tab, but it has been found that satisfactory results can be achieved by positioning the triangle with its apex at about one-third to one-half the way from the base to the tip of the tab. The base of the triangle is spaced from the tip of the tab sufficiently to leave enough material to support the padding layer properly.

The tab 38 thus has a reducing cross-section from its base toward its tip so that it is more flexible towards its tip to achieve a more desirable transition in loading. This provides stability of the portion of the body constrained by the orthotic device, together with comfort at the edge of the orthotic device where there is a transition between the restrained and unrestrained portion of the body.

The panel 52 has notches 54, 56 and 58 in the edge thereof to define tabs 60 and 62. Tabs of this construction are formed all across the bottom edge of the panel 52.

The flexibility of the tabs in this third preferred embodiment is controlled by the molding of ribs integrally with the panel. Ribs 64 and 66 are molded on tab 60 on the side away from the person on whom the orthotic device is to be applied. Two ribs may be applied as shown on tab 60, while a single rib 68 may be applied as shown on tab 62 in FIGS. 5 and 6. FIG. 6 shows the triangular elevation of the rib above the outer surface of the panel. The high point 70 of the rib 66 is about at the bottom of the notches 54 and 56. Thus, the rib inclines downwardly toward the outer surface of the panel 52 from the base of the notch to the tip 72 of rib 60. Thus, from the base of the rib 60 to its tip, there is a decreasing cross section total of the rib and tab. This controls the flexibility of the tab so that it is more flexible toward its tip than toward its base. The portion of the rib on the panel inside of the notches is simply to provide adequate strength to the rib when bending of the tab occurs. This is another way to decrease the cross section of the rib from its base toward its tab to provide greater flexibility of rib so that the flexibility of the rib increases from its base to its tip. FIG. 5 illustrates that one, two or more ribs may be chosen depending upon structural limitations and desired results.

The goal of progressively reducing the stiffness of the tabs from their bases to their tips has been accomplished in the above described species is being a progressive reduction in their cross section of the tabs from base to tip. Another structure which provides the same result is the reduction in bending strength. This is accomplished in the tabs 72 and 74 by making slits or slots through the tabs and across the tabs. Tab 72 has a tip 76 which extends outward from notch, which is the main panel of the orthotic device. A series of slits 80 is cut through the tab 72 and a series of slits 82 is cut through the tab 74, as seen in FIG. 5. The slits are in the same triangular outline as the triangular opening 50. The slits prevent bending stress from passing through the slitted area in a direction at a right angkle to the slits.

This invention has been described in its presently preferred embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An orthotic device comprising:
    a panel for engagement around a body part to be constrained, said panel having an edge with first and second tabs separated by a notch, each of the tabs easier to flex near its tip than near its base, and where such differences in flexion are apparent while the device is being worn; and
    wherein said tab is of substantially uniform thickness and there are openings therein substantially in the configuration of a triangle having its apex towards said base of said tab.

2. The orthotic device of claim 1 further comprising a padding layer on one side of said panel and said tab engages said padding layer.

3. The orthotic device of claim 2 further comprising a tightener structure engaging on each end of said panel.

4. An orthotic device comprising:
    a panel for engagement around a body part to be constrained, said panel having edges and ends, and notches in at least one of said edges to define tabs along that edge, said panel and tabs being made of a synthetic polymer composition material having substantial flexibility while being worn, with said tabs having a base at said notches and a tip away from said base, said panel having an inside surface, a padding layer against said inside surface, said padding layer extending past said edges of said panel, said tabs being configured to have reduced bending strength adjacent said ends of said tabs than towards said base of said tabs said tabs are progressively flexible under load from said padding layer so as to ease the transition between the restrained and unrestrained portion of the body; and
    wherein said panel is of substantially uniform thickness and there is a substantially triangular opening in each of said tabs so that the total cross-section of each of said tabs is progressively lesser towards said tip from said base.

5. The orthotic device of claim 4 wherein said opening is substantially in the configuration of an isosceles triangle having its apex directed towards said base.

6. The orthotic device of claim 5 wherein said panel is stamped from a sheet of synthetic polymer composition material of substantially uniform thickness.

* * * * *